United States Patent
Koehler et al.

(10) Patent No.: US 10,679,762 B2
(45) Date of Patent: Jun. 9, 2020

(54) ANALYZING GRID FOR PHASE CONTRAST IMAGING AND/OR DARK-FIELD IMAGING

(71) Applicant: KONINKLIJKE PHILIPS N.V., Eindhoven (NL)

(72) Inventors: Thomas Koehler, Norderstedt (DE); Roger Steadman Booker, Aachen (DE); Matthias Simon, Eindhoven (NL); Walter Ruetten, Linnich (NL); Herfried Karl Wieczorek, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/307,675

(22) PCT Filed: Jun. 8, 2017

(86) PCT No.: PCT/EP2017/064048
§ 371 (c)(1),
(2) Date: Dec. 6, 2018

(87) PCT Pub. No.: WO2017/212000
PCT Pub. Date: Dec. 14, 2017

(65) Prior Publication Data
US 2019/0304616 A1    Oct. 3, 2019

(30) Foreign Application Priority Data
Jun. 8, 2016  (EP) .................... 16173558

(51) Int. Cl.
*G21K 1/02* (2006.01)
*G01N 23/041* (2018.01)
*A61B 6/00* (2006.01)

(52) U.S. Cl.
CPC ............ *G21K 1/025* (2013.01); *A61B 6/4291* (2013.01); *A61B 6/484* (2013.01); *G01N 23/041* (2018.02);
(Continued)

(58) Field of Classification Search
None
See application file for complete search history.

(56) References Cited

U.S. PATENT DOCUMENTS 5,949,850 A    9/1999  Tang
6,744,052 B1   6/2004  Petersson
(Continued)

OTHER PUBLICATIONS

Wang Dajiang et al., "A Dual Detector Approach for X-Ray Differential Phase Contrast Imaging", Radiation Physics and Chemistry, vol. 95, Dec. 31, 2012 (Dec. 31, 2012), pp. 86-90, XP028793259.
(Continued)

*Primary Examiner* — Hoon K Song
(74) *Attorney, Agent, or Firm* — Larry Liberchuk

(57) ABSTRACT

The invention relates to an analyzing grid for phase contrast imaging and/or dark-field imaging, a detector arrangement for phase contrast imaging and/or dark-field imaging comprising such analyzing grid, an X-ray imaging system comprising such detector arrangement, a method for manufacturing such analyzing grid, a computer program element for controlling such analyzing grid or detector arrangement for performing such method and a computer readable medium having stored such computer program element. The analyzing grid comprises a number of X-ray converting gratings. The X-ray converting gratings are configured to convert incident X-ray radiation into light or charge. The number of X-ray converting gratings comprises at least a first X-ray converting grating and a second X-ray converting grating. Further, the X-ray converting gratings each comprise an array of grating bars, wherein the grating bars within each X-ray converting grating are arranged mutually displaced from each other in a direction perpendicular to the incident X-ray radiation by a specific displacement pitch. Further, the grating bars of the first X-ray converting grating are arranged mutually displaced from the grating bars of the
(Continued)

second X-ray converting grating in the direction perpendicular to the incident X-ray radiation by the displacement pitch divided by the number of X-ray converting gratings.

15 Claims, 5 Drawing Sheets

(52) U.S. Cl.
CPC ...... *A61B 6/4035* (2013.01); *G21K 2207/005* (2013.01)

(56) References Cited

U.S. PATENT DOCUMENTS

| | | | |
|---|---|---|---|
| 2004/0251420 A1* | 12/2004 | Sun | G01T 1/2018 250/370.09 |
| 2005/0270647 A1 | 12/2005 | Polack | |
| 2010/0091947 A1 | 4/2010 | Niu | |
| 2012/0033785 A1* | 2/2012 | Michel | G01N 23/20075 378/21 |
| 2012/0236985 A1* | 9/2012 | Schusser | G21K 1/06 378/16 |
| 2013/0223595 A1* | 8/2013 | Vogtmeier | A61B 6/06 378/62 |
| 2014/0112440 A1 | 4/2014 | David | |
| 2014/0177795 A1 | 6/2014 | Spahn | |
| 2015/0177390 A1 | 6/2015 | Mattson | |

OTHER PUBLICATIONS

Rutishauser Simon et al., "Structured Scintillator for Hard X-Ray Grating Interferometry", Applied Physics Letters, A 1 P Publishing LLC, US, vol. 98, No. 17, Apr. 27, 2011 (Apr. 27, 2011), pp. 171107-1-171107-3, XP012140442.

* cited by examiner

ANALYZING GRID FOR PHASE CONTRAST IMAGING AND/OR DARK-FIELD IMAGING

FIELD OF THE INVENTION

The invention relates to an analyzing grid for phase contrast imaging and/or dark-field imaging, a detector arrangement for phase contrast imaging and/or dark-field imaging comprising such analyzing grid, an X-ray imaging system comprising such detector arrangement, a method for manufacturing such analyzing grid, a computer program element for controlling such analyzing grid or detector arrangement for performing such method and a computer readable medium having stored such computer program element.

BACKGROUND OF THE INVENTION

X-ray imaging is applied in various technical fields in order to obtain information about internal structures within a region of interest of an object. For example, medical X-ray imaging devices are used to obtain information about internal structures within a patient's body. Phase contrast imaging, e.g. using an interferometer, has been developed to provide higher contrast, especially in soft tissue and other low-absorbing materials. At the same time, the interferometer may also yield a dark-field signal, related to small-angle scattering from structures smaller than the spatial resolution of the detector. The phase information may be acquired using a phase stepping method, which may require multiple exposures.

Phase contrast imaging requires phase-stepping, i.e. a phase grating is scanned along in order to retrieve phase information. That is, several projections are acquired for different positions of the grating. Phase contrast imaging procedures therefore require significantly more time when compared to conventional X-ray applications. Furthermore, the required use of an absorption grid or structured scintillator implies that a considerable amount of X-ray photons passing a patient are discarded, resulting in a poor X-ray dose efficiency. For example, US 2014/0177795 A1 describes an electronic phase stepping method for acquiring the phase information. Also WANG DAJIANG ET AL: "A dual detector approach for X-ray differential phase contrast imaging", RADIATION PHYSICS AND CHEMISTRY, vol. 95, 31 Dec. 2012 (2012-12-31), pages 86-90, XP028793259, ISSN: 0969-806X, 001: 10.1016/J.RAD-PHYSCHEM.2012.12.027 and RUTISHAUSER SIMON ET AL: "Structured scintillator for hard x-ray grating interferometry", APPLIED PHYSICS LETTERS, A 1 P PUBLISHING LLC, US, vol. 98, no. 17, 27 Apr. 2011 (2011-04-27), pages 171107-1-171107-3, XP012140442, ISSN: 0003-6951, 001: 10.1063/1.3583464 refer to this field.

SUMMARY OF THE INVENTION

Hence, there may be a need to provide an improved grid for phase contrast imaging and/or dark-field imaging, which allows to increase the X-ray dose efficiency during X-ray image acquisition.

The problem of the present invention is solved by the subject-matters of the independent claims, wherein further embodiments are incorporated in the dependent claims. It should be noted that the aspects of the invention described in the following apply also to the analyzing grid for phase contrast imaging and/or dark-field imaging, the detector arrangement for phase contrast imaging and/or dark-field imaging comprising such analyzing grid, the X-ray imaging system comprising such detector arrangement, the method for manufacturing such analyzing grid, the computer program element for controlling such analyzing grid or detector arrangement for performing such method and the computer readable medium having stored such computer program element.

According to the present invention, an analyzing grid for phase contrast imaging and/or dark-field imaging is presented. The analyzing grid comprises a number of X-ray converting gratings. The X-ray converting gratings are configured to convert incident X-ray radiation into light or charge. The number of X-ray converting gratings comprises at least a first X-ray converting grating and a second X-ray converting grating. Optionally, the X-ray converting gratings are stacked in a direction parallel to the incident X-ray radiation.

Further, the X-ray converting gratings each comprise an array of grating bars, wherein the grating bars within each X-ray converting grating are arranged mutually displaced from each other in a direction perpendicular to the incident X-ray radiation by a specific displacement pitch. In other words, the displacement pitch is the distance of the center lines of two adjacent grating bars of the same, e.g. the first X-ray converting grating.

Further, the grating bars of the first X-ray converting grating are arranged mutually displaced from the grating bars of the second X-ray converting grating in the direction perpendicular to the incident X-ray radiation by the displacement pitch divided by the number of X-ray converting gratings.

In other words, a staggered stack of at least a first X-ray converting grating and a second X-ray converting grating is presented. For example, two X-ray converting gratings can be stacked with half the displacement pitch with respect to each other, i.e. the lower X-ray converting grating has grating bars placed at the same positions where the upper X-ray converting grating has an X-ray transparent material. An amount of two X-ray converting gratings can be understood as two simultaneous samples of the phase stepping and the acquisition speed may therefore be doubled.

The staggered configuration implies that almost every photon that traversed a patient is accounted for and thereby increases the X-ray dose efficiency. For a thickness of e.g. about 200 μm of the X-ray transparent material (e.g. silicon) and an energy range of e.g. about 60 keV, over 98% of photons may be transmitted through. In other words, due to the displacement pitch divided by the number of X-ray converting gratings, practically all photons that traversed a patient and which would otherwise have been partially discarded are received.

In an example, the number of X-ray converting gratings further comprises a third X-ray converting grating. The grating bars of each of the first, second and third X-ray converting gratings are then arranged mutually displaced from the grating bars of the other two X-ray converting gratings by a third of the displacement pitch. In other words, when taking the concept of a staggered stack of at least a first X-ray converting grating and a second X-ray converting grating further to three or more X-ray converting gratings, a correspondingly larger number of phase stepping samples can be acquired simultaneously. With three of more staggered X-ray converting gratings, it is further possible to avoid the process of mechanic or electronic phase stepping and to obtain phase contrast images with a single X-ray exposure and image acquisition. In other words, three or more layers may be used to end the need for mechanic or electronic phase stepping altogether. In a three stack layer arrangement for example, each X-ray converting grating may have a spatial duty cycle of 33.3% to avoid overlapping of X-ray converting gratings. This can be extended to as many layers as it might be required.

The X-ray converting grating may be placed on top of an optical detector (i.e. photodiode array or charge coupled device). The detector may be made of silicon to have only a negligible absorption and attenuation. Measures may be taken by design to minimize direct detection and radiation damage, e.g. by using organic photodiodes made of very thin and light weight material.

Exemplarily, the X-ray converting grating may be a structured scintillator comprising scintillator slabs as grating bars.

In an example, the X-ray converting gratings comprising grating bars are made of at least one material of the group of $Gd_2O_2S$:Pr, $Gd_2O_2S$:Ce, CsI:Tl, Ce-doped perovskites, cerium doped (yttrium-gadolinium-lutetium) based (gallium-aluminium) garnets, e.g. LuAG ($Lu_3Al_5O_{12}$), GGAG ($Gd_3(Ga,Al)_5O_{12}$), YAG ($Y_3Al_5O_{12}$); bismuth germanate ($Bi_3Ge_4O_{12}$), yttrium gadolinium oxide $(Y,Gd)_2O_3$:Eu, and similar suited compounds like $Lu_2O_3$:Eu and solid solutions of Y, Gd and Lu (in any combination) doped with $Eu_3$+. Also hygroscopic materials can be used, as e.g. CsI:Na, NaI:Tl, or $SrI_2$:Eu. Further, cubic materials may be used in thin transparent ceramic layers to enable an easy transfer of a signal to a detector. The at least first and second X-ray converting gratings may or may not be of the same material.

The grating bars may be provided with reflector material on their walls to maximize a light or charge output towards the detector.

Exemplarily, each of the number of X-ray gratings is arranged on one of an equal number of detectors, wherein the detectors are configured to detect the light or charge converted by the respective X-ray converting grating. In other words, each X-ray converting grating is arranged on a detector. The grating bars may be separated by spacers. As spacer material light elements may be used, as e.g. silicon, aluminum, aluminum oxide ceramics, polymers, etc. Silicon is a good choice as it can be structured (e.g. etched) in fine pitch. In an example, the first X-ray converting grating and the second X-ray converting grating are arranged between two detectors, wherein the detectors are configured to detect the light or charge converted by the respective X-ray converting grating. In other words, the first X-ray converting grating and the second X-ray converting grating may be placed between two detectors, the first detector below detecting the light or charge output coming from above from of the first X-ray converting grating and the second detectors above detecting light or charge output coming from below from the second X-ray converting grating.

In an example, the first X-ray converting grating and the second X-ray converting grating are arranged essentially next to each other in the direction perpendicular to the incident X-ray radiation, wherein the X-ray converting gratings comprise reflector walls. The wording "next to each other" may be understood as interleaved or interdigitated. Then, the staggering of the X-ray converting gratings in the direction parallel to the incident X-ray radiation is implemented in that the reflector walls are arranged at upper face sides and omitted at lower face sides of the first X-ray converting grating and in that the reflector walls arranged at lower face sides and omitted at upper face sides of the second X-ray converting grating.

The X-ray converting gratings may then be composed of only grating bars and their corresponding reflector walls. No passive spacer may be used. That is, the grating bars of the first X-ray converting grating may have reflector elements on all of their walls with the exception of the bottom side. Similarly, the grating bars of the second X-ray converting grating may have reflector elements on all walls with the exception of the top side opposite to the bottom side.

In an example, the first X-ray converting grating and the second X-ray converting grating overlap partially in the direction parallel to the incident X-ray radiation. Then, the grating bars may be arranged above each other and next to each other in such a way that they do overlap in the direction parallel to the incident X-ray radiation or in the direction along the thickness of the structure. Overlapping means that the grating bars of the first X-ray converting grating and the second X-ray converting grating are equally long but do not start and end at the same positions in the direction parallel to the incident X-ray radiation.

In an example, the X-ray converting gratings are spaced apart from each other in the direction parallel to the incident X-ray radiation by a spacer. Then, the grating bars may be arranged above each other and not next to each other in such a way that they do not overlap in the direction parallel to the incident X-ray radiation or in the direction along the thickness of the structure. The silicon spacer material between the grating bars may be made correspondingly thicker. Then, the X-ray photons always encounter X-ray converting material along their path and are not lost in the e.g. silicon spacer material.

In an example, at least some of the grating bars or scintillator slabs are provided with a discontinuous cross section when seen in the direction parallel to the incident X-ray radiation to contribute to spatial filtering. The discontinuous cross section may be a trapezoidal cross-section forming a tapered cavity between a grating bar and its adjacent grating bar. Also other forms of cross section are possible. Exemplarily, the grating bars may be provided with a continuous and e.g. rectangular cross section when seen in the direction parallel to the incident X-ray radiation.

In an example, the first X-ray converting grating forms a scintillator and the second X-ray converting grating forms an anti-scatter grid. The two X-ray converting gratings may be built in an interleaved manner on opposing sides of a wafer. Putting both X-ray converting gratings on one wafer makes it possible align the two X-ray converting gratings very accurately as e.g. holes or markers can be used to position the wafer during the process of e.g. etching the X-ray converting gratings into the wafer. Consequently, a problem of radiation exposure to electronics is resolved and it is ensured that there is no loss of direct radiation by the anti-scatter grid as the anti-scatter grid blocks only the direct radiation that is not supposed to be detected.

In an example, the first X-ray converting grating forms a direct conversion anode and the second X-ray converting grating forms a direct conversion cathode. Exemplarily, the anode or first X-ray converting grating and the cathode or second X-ray converting grating may be arranged between two detectors with alternating grating bars to form an interleaved arrangement of cathode and anode.

The direct conversion anode and the direct conversion cathode may be made of the same material, e.g. a single bulk (CdTe, CZT, etc.), separated from each other by electrically isolated walls. The direct conversion anode and the direct conversion cathode may comprise individual grating bars of e.g. perovskites or any other high-Z semiconductor material with electrically isolated side walls.

Alternatively, different types of direct conversion materials (e.g. n-type Si and p-type GaAs) may alternate to thereby achieve that electric field lines are arranged along the same direction (e.g. hole signal on Si and electron signal on GaAs). The detectors shall then provide an adequate bias voltage with different polarity of the bias on each side.

Exemplarily, the grating bars of one of the first and second X-ray converting gratings may be interconnected to form a common cathode. The grating bars of the other of the first and second X-ray converting gratings forming the anode may be connected to their corresponding detector pixels e.g. with several gratings per detector pixel.

Alternatively, the common cathode is placed at a top surface and the anode portions are structured on a bottom surface of the device opposite to the top surface. This configuration allows using a single bulk of direct conversion material (e.g. CZT, CdTe, GaAs, Perovskites, PbO, etc.). Further, only one detector is required, which captures independent signals from different anode portions.

The structuring of the anode and the detector pixels can be made in that different anode "slabs" are comprised within an equivalent detector pixel (e.g. 3 to 4 anode "slabs" per 150 μm detector pixel). Each detector pixel then collects a signal resulting from a charge induced of two equivalent anode contacts spatially distributed.

In all embodiments above, cross-sections have been shown to depict a detector stack. It's understood that the detector may be arranged on either 1D or 2D configuration. For the 2D case, a fine pitch may only be required along one direction (x) while on the other (y) the pitch is the same as the native detector pitch.

According to the present invention, also a detector arrangement for phase contrast imaging and/or dark-field imaging is presented. The detector arrangement comprises an analyzing grid as described above and at least a detector configured to detect the light or charge converted by an X-ray converting grating of the analyzing grid.

According to the present invention, also an X-ray imaging system comprising an X-ray source and a detector arrangement as described above is presented. The X-ray source is configured to apply X-ray radiation to an object of interest to be detected by the detector arrangement. The X-ray imaging system may further comprise a source grating $G_0$ arranged between the X-ray source and the object and a grating $G_1$ arranged either in front or behind the object. Above described analyzing grid of the detector arrangement may be arranged as grating $G_2$ behind the grating $G_1$.

According to the present invention, also a method for manufacturing an analyzing grid is presented. It comprises the following steps:

structuring a number of wafers to obtain an array of grating bars in each wafer, and filling a space between the grating bars with X-ray converting material to obtain a number of X-ray converting gratings.

The X-ray converting gratings are configured to form an analyzing grid as described above. Silicon may be used as wafer material. The structuring of the wafer may be done by etching.

The structuring of the wafer may be done from both sides. Also the filling with the X-ray converting material can then be done from both sides.

In an example, the structuring by e.g. etching and the filling with the X-ray converting material is done from only a first side of the wafer. After etching and filling, the wafer may be grinded to reveal the X-ray converting gratings from e.g. the top side. Afterwards reflector material may be deposited to alternate grating bars on both sides. The trenches may have different depths, thereby only revealing one type of X-ray converting grating after grinding. This may simplify a surface treatment (e.g. a reflector structuring) on one of the sides.

Above mentioned example of X-ray converting gratings spaced apart from each other in the direction parallel to the incident X-ray radiation by a spacer may be achieved by a further manufacturing step of attaching two X-ray converting gratings to each other by connecting their second sides not being used for structuring and filling. The wafer may be etched from only one side and afterwards two of such structured X-ray converting gratings may be attached and e.g. glued or wafer fused back-to-back with a half pitch shift.

According to the present invention, also a computer program element is presented, wherein the computer program element comprises program code means for causing the analyzing grid or the detector arrangement as defined in the independent claims to carry out the steps of an imaging method when the computer program is run on a computer controlling an imaging system.

It shall be understood that the analyzing grid for phase contrast imaging and/or dark-field imaging, the detector arrangement for phase contrast imaging and/or dark-field imaging comprising such analyzing grid, the method for manufacturing such analyzing grid, the computer program element for controlling such analyzing grid or detector arrangement for performing such method and the computer readable medium having stored such computer program element according to the independent claims have similar and/or identical preferred embodiments, in particular, as defined in the dependent claims. It shall be understood further that a preferred embodiment of the invention can also be any combination of the dependent claims with the respective independent claim.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the accompanying drawings.

DETAILED DESCRIPTION OF EMBODIMENTS

Figure 1:
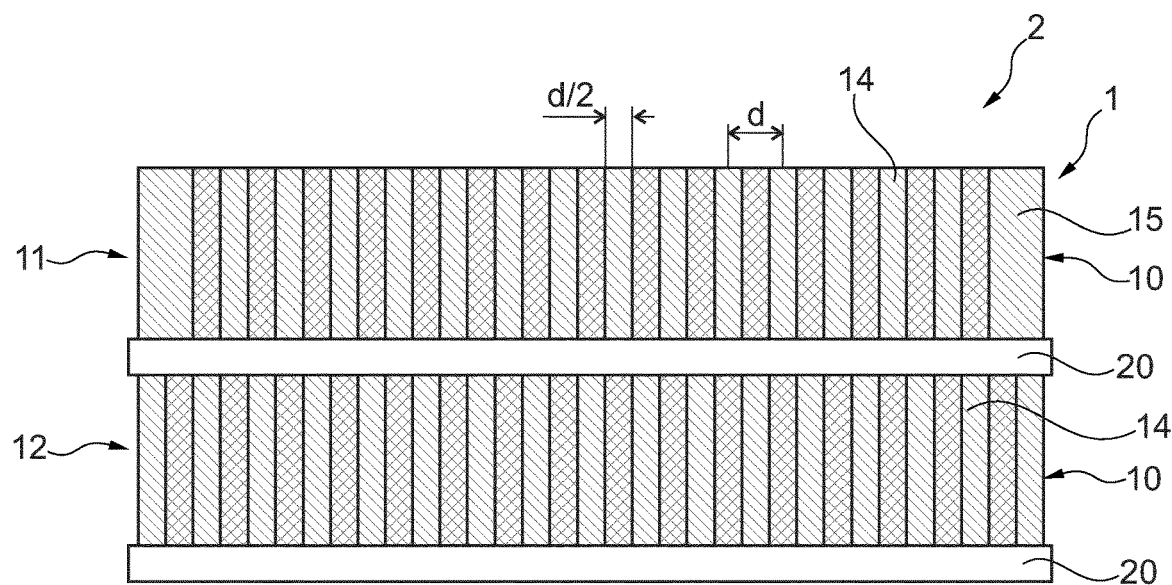
FIG. 1 shows schematically and exemplarily an embodiment of a detector arrangement for phase contrast imaging and/or dark-field imaging according to the invention.

FIG. 1 shows schematically and exemplarily an embodiment of a detector arrangement for phase contrast imaging and/or dark-field imaging according to the invention. The detector arrangement 2 comprises an analyzing grid 1.

The analyzing grid 1 comprises here two of X-ray converting gratings 10, namely a first X-ray converting grating 11 and a second X-ray converting grating 12. The X-ray converting gratings 10 convert incident X-ray radiation into light or charge. Here, the X-ray converting grating is a structured scintillator comprising scintillator slabs as grating bars 14.

The X-ray converting gratings 10 are stacked in a direction parallel to the incident X-ray radiation. The X-ray converting gratings 10 each comprise an array of grating bars 14 made of e.g. CsI. The grating bars 14 are separated by spacers 15 of e.g. silicon.

The grating bars 14 within each X-ray converting grating are arranged mutually displaced from each other in a direction perpendicular to the incident X-ray radiation (coming from above in FIG. 1) by a specific displacement pitch d. The displacement pitch d is the distance of the center lines of two adjacent grating bars 14.

The grating bars 14 of the first X-ray converting grating 11 are arranged mutually displaced from the grating bars 14 of the second X-ray converting grating 12 in the direction perpendicular to the incident X-ray radiation by the displacement pitch d divided by the number of X-ray converting gratings 10, here two, which means d/2.

Each of the first X and the second X-ray converting gratings 10 are placed on top of optical detectors 20, here two photodiode arrays. The detectors 20 are here configured to detect the light converted by the respective X-ray converting grating.

As a result, a staggered arrangement of the first X-ray converting grating 11 and the second X-ray converting grating 12 is presented. The two X-ray converting gratings 10 are staggered with half a displacement pitch with respect to each other, i.e. the lower second X-ray converting grating has grating bars 14 placed at the same positions where the upper first X-ray converting grating 11 has an X-ray transparent material.

Figure 2:
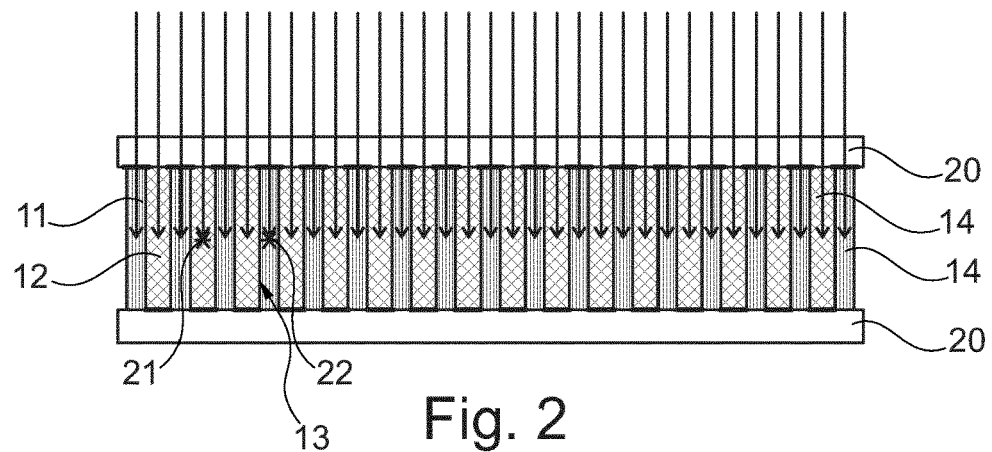
FIG. 2 shows schematically and exemplarily another embodiment of a detector arrangement for phase contrast imaging and/or dark-field imaging according to the invention.

FIG. 2 shows schematically and exemplarily another embodiment of a detector arrangement 2 for phase contrast imaging and/or dark-field imaging according to the invention. Here, the first X-ray converting grating 11 and the second X-ray converting grating 12 are arranged between two detectors 20. In detail, the first X-ray converting grating 11 and the second X-ray converting grating 12 are placed between two detectors 20, the first detector below detecting the light or charge output coming from above from of the first X-ray converting grating 11 and the second detector above detecting light or charge output coming from below from the second X-ray converting grating 12.

The first X-ray converting grating 11 and the second X-ray converting grating 12 are arranged next to each other in the direction perpendicular to the incident X-ray radiation (marked by arrows in FIG. 2). The X-ray converting gratings 10 comprise reflector walls 13. The staggering of the X-ray converting gratings 10 in the direction parallel to the incident X-ray radiation is implemented in that the reflector walls 13 are arranged at upper face sides and omitted at lower face sides of the first X-ray converting grating 11 and in that the reflector walls 13 arranged at lower face sides and omitted at upper face sides of the second X-ray converting grating 12. In other words, the grating bars 14 of the first X-ray converting grating 11 have reflector elements on all of their walls with the exception of the bottom side. Similarly, the grating bars 14 of the second X-ray converting grating 12 have reflector elements on all walls with the exception of the top side. As a result, the X-ray converting gratings 10 are here composed of only grating bars 14 and their corresponding reflector walls 13. No passive spacer is used.

For example, light generated at a conversion point 22 may propagate in all directions, but is only collected by the upper detector 20 as the other directions are limited by the reflector walls 13 arranged at the lower face side and at the lateral sides. Correspondingly, light generated at a conversion point 21 will reach only the lower detector 20 as there are reflecting walls 13 at the upper face side and at the lateral sides.

Figure 3:
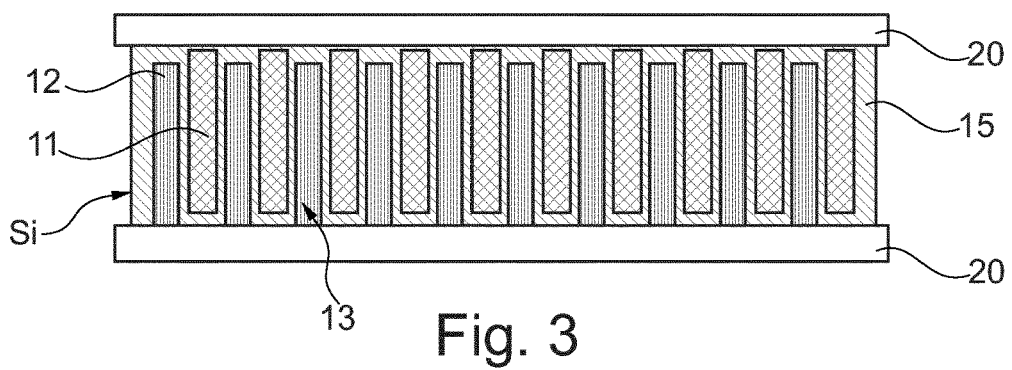
FIG. 3 shows schematically and exemplarily another embodiment of a detector arrangement for phase contrast imaging and/or dark-field imaging according to the invention.

FIG. 3 shows schematically and exemplarily another embodiment of a detector arrangement 2 for phase contrast imaging and/or dark-field imaging according to the invention. Here, the first X-ray converting grating 11 and the second X-ray converting grating 12 overlap partially in the direction parallel to the incident X-ray radiation. In other words, the grating bars 14 are arranged above each other and next to each other in such a way that they do overlap in the direction parallel to the incident X-ray radiation or in the direction along the thickness of the structure. As shown in FIG. 3, overlapping means that the grating bars 14 of the first X-ray converting grating 11 and the second X-ray converting grating 12 are equally long but do not end at the same positions. The X-ray converting gratings 10 again comprise reflector walls 13 and are separated by spacers 15.

Figure 4:
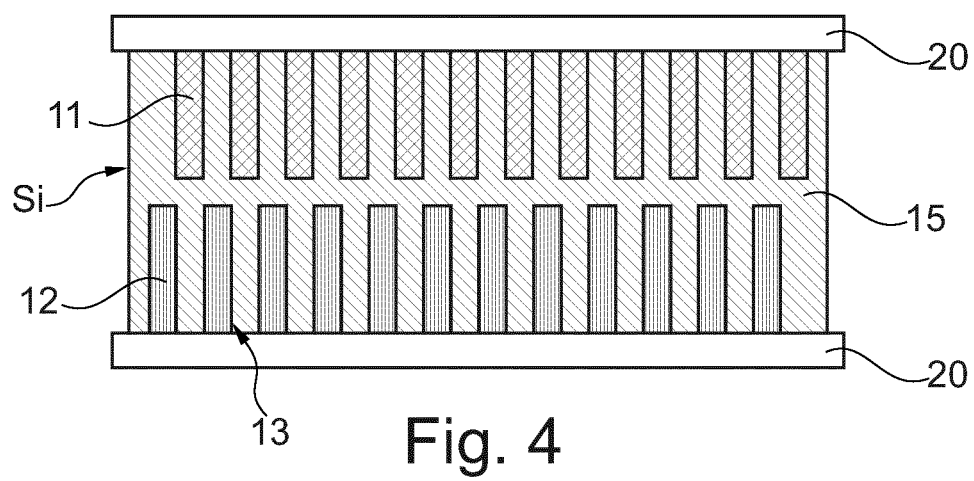
FIG. 4 shows schematically and exemplarily another embodiment of a detector arrangement for phase contrast imaging and/or dark-field imaging according to the invention.

FIG. 4 shows schematically and exemplarily another embodiment of a detector arrangement 2 for phase contrast imaging and/or dark-field imaging according to the invention. Here, the X-ray converting gratings 10 are spaced apart from each other in the direction parallel to the incident X-ray radiation by a spacer. In other words, the grating bars 14 are arranged above each other and not next to each other in such a way that they do not overlap in the direction parallel to the incident X-ray radiation or in the direction along the thickness of the structure. Further, the spacers 15 between the grating bars 14 are thicker, so that the X-ray photons always encounter X-ray converting material along their path and are not lost in the spacer 15. The X-ray converting gratings 10 again comprise reflector walls 13. The first X-ray converting grating 11 and the second X-ray converting grating 12 are arranged between two detectors 20.

Figure 5:
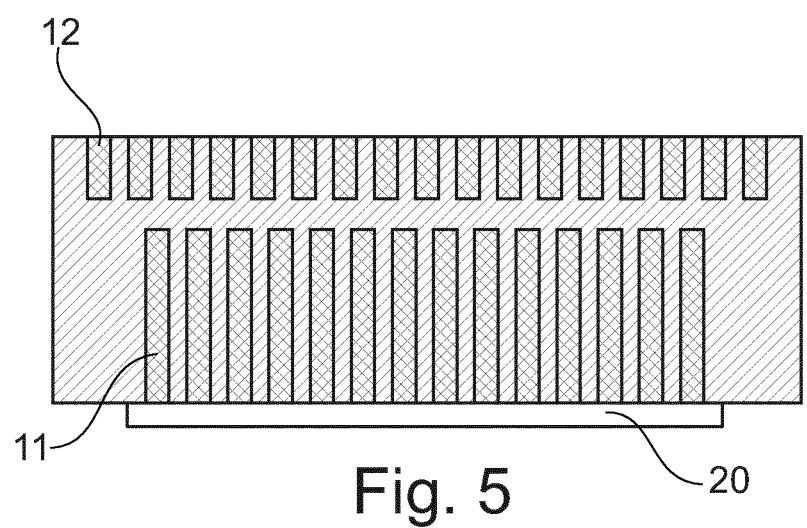
FIG. 5 shows schematically and exemplarily another embodiment of a detector arrangement for phase contrast imaging and/or dark-field imaging according to the invention.

FIG. 5 shows schematically and exemplarily another embodiment of a detector arrangement 2 for phase contrast imaging and/or dark-field imaging according to the invention. Here, the first X-ray converting grating 11 forms a scintillator and the second X-ray converting grating 12 forms an anti-scatter grid. The two X-ray converting gratings 10 are built in an interleaved manner on opposing sides of a carrier or wafer made of e.g. silicon. The first X-ray converting grating 11 or scintillator is arranged on a detector 20.

Figure 6:
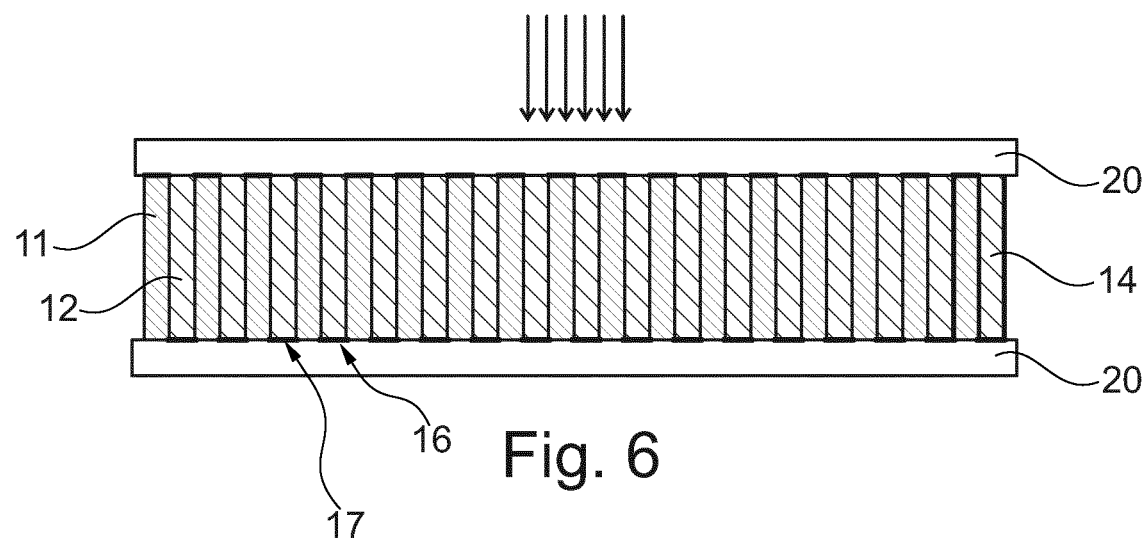
FIG. 6 shows schematically and exemplarily another embodiment of a detector arrangement for phase contrast imaging and/or dark-field imaging according to the invention.

FIG. 6 shows schematically and exemplarily another embodiment of a detector arrangement 2 for phase contrast imaging and/or dark-field imaging according to the invention. Here, the first X-ray converting grating 11 forms a direct conversion anode 16 and the second X-ray converting grating 12 forms a direct conversion cathode 17. The anode 16 or first X-ray converting grating 11 and the cathode 17 or second X-ray converting grating 12 are arranged between two detectors 20. The grating bars 14 of the first X-ray converting grating 11 and the second X-ray converting grating 12 are alternating to form an interleaved arrangement of cathode 17 and anode 16.

The opposite side of the anode 16 acts as cathode common to all anodes 16. Likewise, the opposite side of the cathode 17 acts as anode. Each detector 20 is configured to detect electrons or holes. That is, if the direct converter is electron collection (e.g. CZT, CdTe . . . ), the bottom detector collects electrons from the anode 16 and the top detector collects electrons from the anode opposite to the cathode 17. The common cathodes in this case are adequately biased to the required potential. This bias is provided by the "opposite" detector. That is, the bottom detector for the anode 16 provides a cathode bias, wherein a signal is collected from the anode opposite to the cathode 17 from top detector. Similarly, if the detector is hole collection. The direct conversion anode 16 and the direct conversion cathode 17 are here made of the same material, e.g. a single bulk, separated from each other by electrically isolated walls.

Figure 7:
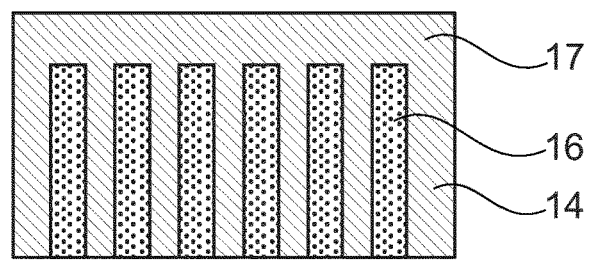
FIG. 7 shows schematically and exemplarily another embodiment of a detector arrangement for phase contrast imaging and/or dark-field imaging according to the invention.

FIG. 7 shows schematically and exemplarily another embodiment of a detector arrangement 2 for phase contrast imaging and/or dark-field imaging according to the invention. FIG. 7 shows the electrode structure from the bottom. Here, the grating bars 14 of one of the first and second X-ray converting gratings 10 are interconnected to form a common cathode 17. The grating bars 14 of the other of the first and second X-ray converting gratings 10 forming the anode 16 are connected to their corresponding detector pixels.

Figure 8:
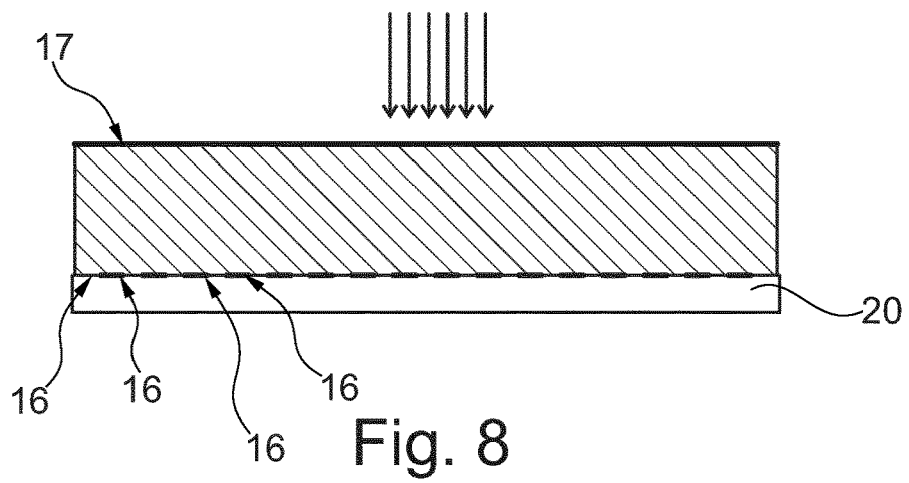
FIG. 8 shows schematically and exemplarily another embodiment of a detector arrangement for phase contrast imaging and/or dark-field imaging according to the invention.

FIG. 8 shows schematically and exemplarily another embodiment of a detector arrangement 2 for phase contrast imaging and/or dark-field imaging according to the invention. Here, the common cathode 17 is placed at a top surface and the anode portions 16 are structured on a bottom surface of the device. This configuration allows using a single bulk of direct conversion material and requires only one detector capturing independent signals from different anode portions 16.

Figure 9:
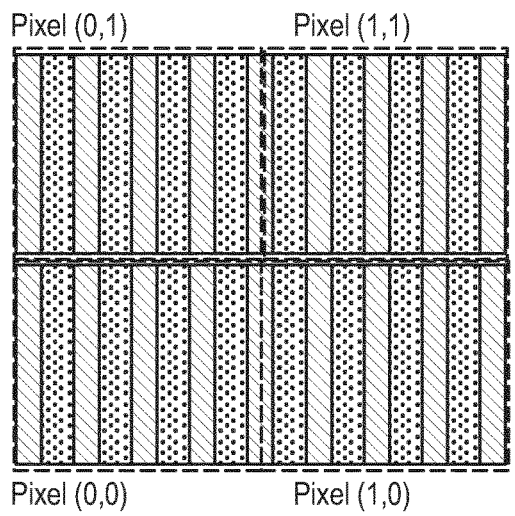
FIG. 9 shows schematically and exemplarily a structuring of the anode on the left and of the detector pixels on the right.
Figure 9:
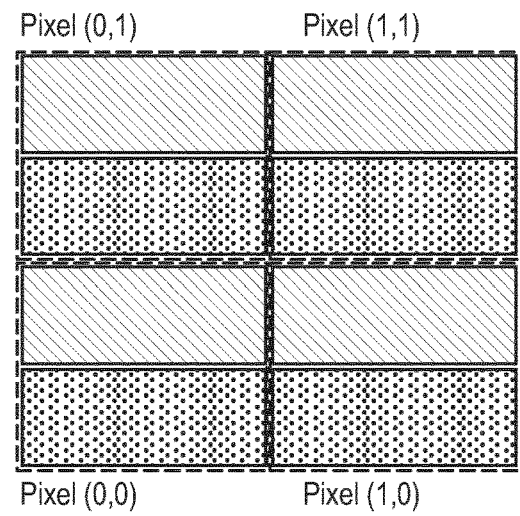

FIG. 9 shows schematically and exemplarily a structuring of the anode 16 on the left and of the detector pixels on the right. Different anode "slabs" are comprised within an equivalent detector pixel. Each detector pixel then collects a signal resulting from a charge induced of two equivalent anode contacts spatially distributed.

Figure 10:
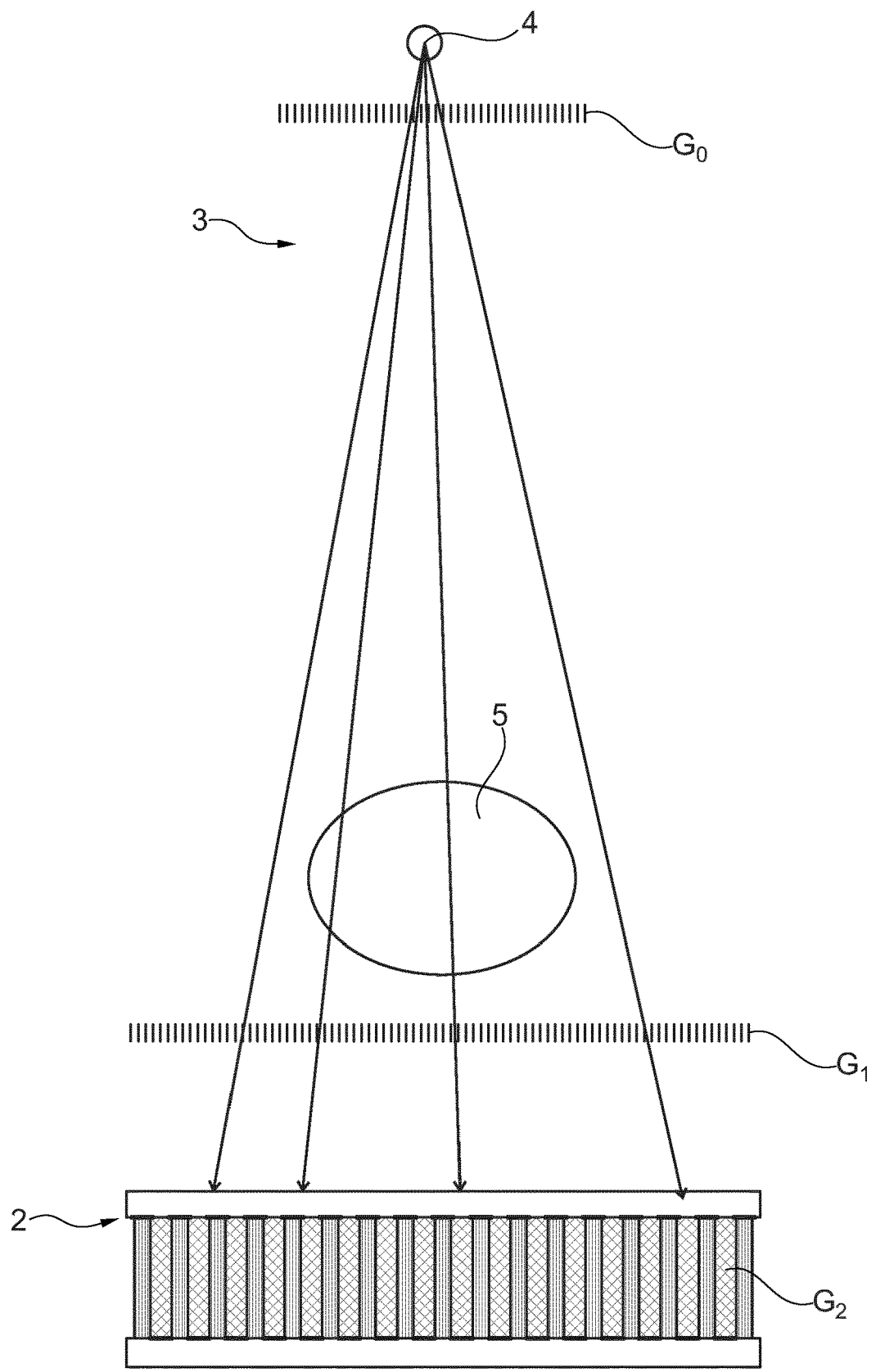
FIG. 10 shows schematically and exemplarily an X-ray imaging system according to the invention.

FIG. 10 shows schematically and exemplarily an X-ray imaging system 3 according to the invention. It comprises an X-ray source 4 and a detector arrangement 2 as described above. The X-ray source 4 applies X-ray radiation to an object 5 of interest to be detected by the detector arrangement 2. The X-ray imaging system 3 here comprises a source grating $G_0$ arranged between the X-ray source 4 and the object 5, a first grating $G_1$ arranged behind the object 5 and the analyzing grid of the detector arrangement 2 as grating $G_2$ arranged behind grating $G_1$. Note that this is not drawn to scale as the fan angle of the X-ray radiation is too large for the shown grating $G_2$ (the X-rays actually hit the detector arrangement 2 almost perpendicularly).

Figure 11:
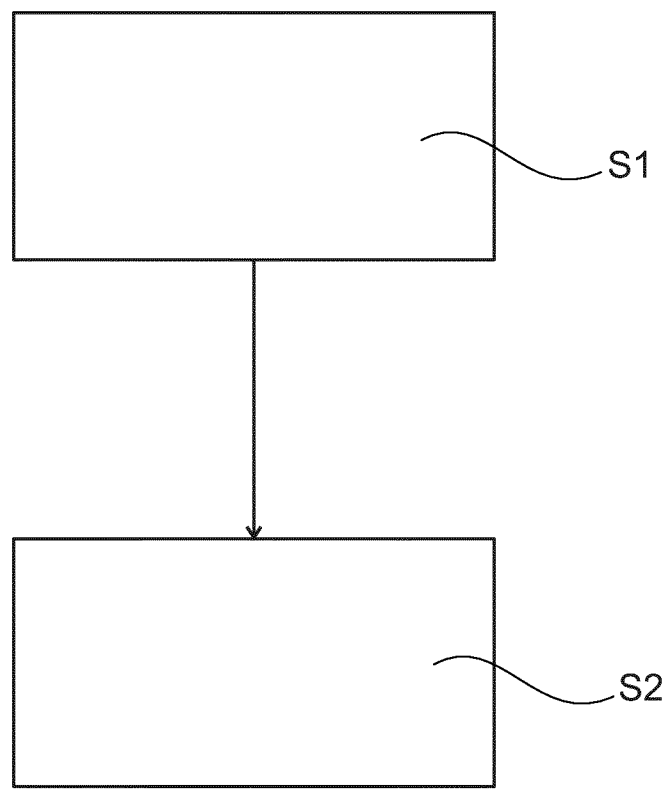
FIG. 11 shows basic steps of an example of a method for manufacturing an analyzing grid.

FIG. 11 shows a schematic overview of steps of a method for manufacturing an analyzing grid 1. The method comprises the following steps, not necessarily in this order:

In a first step S1, structuring a number of wafers to obtain an array of grating bars 14 in each wafer.

In a second step S2, filling a space between the grating bars 14 with X-ray converting material to obtain a number of X-ray converting gratings 10.

The X-ray converting gratings 10 are configured to form an analyzing grid 1 as described above.

In another exemplary embodiment of the present invention, a computer program or a computer program element is provided that is characterized by being adapted to execute imaging method steps on an appropriate system.

The computer program element might therefore be stored on a computer unit, which might also be part of an embodiment of the present invention. This computing unit may be adapted to perform or induce a performing of the steps of an imaging method. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it, which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An analyzing grid for phase contrast imaging and/or dark-field imaging, comprising a number of X-ray converting gratings,
    wherein the X-ray converting gratings are configured to convert incident X-ray radiation into light or charge,
    wherein the X-ray converting gratings comprise at least a first X-ray converting grating and a second X-ray converting grating,
    wherein each of the X-ray converting gratings comprises an array of grating bars,
    wherein the grating bars within each of the X-ray converting gratings are arranged mutually displaced from each other in a direction perpendicular to an incident X-ray radiation by a specific displacement pitch, which is a distance between center lines of two adjacent grating bars,
    wherein the grating bars of the first X-ray converting grating are arranged mutually displaced from the grating bars of the second X-ray converting grating in the direction perpendicular to the incident X-ray radiation, and
    wherein the first X-ray converting grating and the second X-ray converting grating are arranged between two detectors configured to detect light or charge converted by the respective first and second X-ray converting gratings.

2. The analyzing grid according to claim 1, wherein the grating bars of the first X-ray converting grating are arranged mutually displaced from the grating bars of the second X-ray converting grating in the direction perpendicular to the incident X-ray radiation by the displacement pitch divided by a number of X-ray converting gratings.

3. The analyzing grid according to claim 1, wherein the first X-ray converting grating and the second X-ray converting grating overlap partially in the direction parallel to the incident X-ray radiation.

4. The analyzing grid according to claim 1, wherein the X-ray converting gratings are spaced apart from each other in the direction parallel to the incident X-ray radiation by a spacer.

5. The analyzing grid according to claim 1, wherein the first X-ray converting grating and the second X-ray converting grating are arranged substantially next to each other in the direction perpendicular to the incident X-ray radiation, wherein the X-ray converting gratings comprise reflector walls, and wherein a staggering of the X-ray converting gratings in the direction parallel to the incident X-ray radiation is implemented by the reflector walls arranged at upper face sides and omitted at lower face sides of the first X-ray converting grating and by the reflector walls arranged at lower face sides and omitted at upper face sides of the second X-ray converting grating.

6. The analyzing grid according to claim 1, wherein the first X-ray converting grating forms a scintillator, and the second X-ray converting grating forms an anti-scatter grid.

7. The analyzing grid according to claim 1, wherein a number of X-ray converting gratings further comprises a third X-ray converting grating, and wherein the grating bars of each of the three X-ray converting gratings are arranged mutually displaced from the grating bars of the other two X-ray converting gratings by a third of the displacement pitch.

8. The analyzing grid according to claim 1, wherein at least some of the grating bars are provided with a discontinuous cross section when seen in the direction parallel to the incident X-ray radiation.

9. The analyzing grid according to claim 1, wherein the X-ray converting gratings are made of at least one material comprising CsI:Tl, Ce-doped perovskites, cerium doped (yttrium-gadolinium-lutetium) based (gallium-aluminium) garnets, bismuth germanate, yttrium gadolinium oxide, solid solutions of Y, Gd and/or Lu doped with Eu3+, CsI:Na, NaI:Tl, and SrI2.

10. The analyzing grid according to claim 1, wherein the first X-ray converting grating forms a direct conversion anode, and the second X-ray converting grating forms a direct conversion cathode, wherein the grating bars of the second X-ray converting grating are interconnected to form a common cathode for a detector.

11. The analyzing grid according to claim 10, wherein the direct conversion anode and the direct conversion cathode are made of substantially same material separated from each other by electrically isolated walls.

12. An X-ray imaging system, comprising:
    an X-ray source, and
    an analyzing grid for phase contrast imaging and/or dark-field imaging, comprising a number of X-ray converting gratings,
        wherein the X-ray converting gratings are configured to convert incident X-ray radiation into light or charge,
        wherein the X-ray converting gratings comprise at least a first X-ray converting grating and a second X-ray converting grating,
        wherein each of the X-ray converting gratings comprises an array of grating bars,
        wherein the grating bars within each of the X-ray converting gratings are arranged mutually displaced from each other in a direction perpendicular to an incident X-ray radiation by a specific displacement pitch, which is a distance between center lines of two adjacent grating bars,
        wherein the grating bars of the first X-ray converting grating are arranged mutually displaced from the grating bars of the second X-ray converting grating in the direction perpendicular to the incident X-ray radiation, and
        wherein the first X-ray converting grating and the second X-ray converting grating are arranged between two detectors configured to detect light or charge converted by the respective first and second X-ray converting gratings, wherein the X-ray source is configured to apply X-ray radiation to an object to be detected by the detectors.

13. A method for manufacturing an analyzing grid, comprising:
structuring a number of wafers to obtain an array of grating bars in each wafer, and
filling a space between the grating bars with X-ray converting material to obtain a number of X-ray converting gratings,
wherein the X-ray converting gratings are configured to form an analyzing grid for phase contrast imaging and/or dark-field imaging,
wherein the X-ray converting gratings are configured to convert incident X-ray radiation into light or charge,
wherein the X-ray converting gratings comprise at least a first X-ray converting grating and a second X-ray converting grating,
wherein each of the X-ray converting gratings comprises the array of grating bars,
wherein the grating bars within each of the X-ray converting gratings are arranged mutually displaced from each other in a direction perpendicular to an incident X-ray radiation by a specific displacement pitch, which is a distance between center lines of two adjacent grating bars,
wherein the grating bars of the first X-ray converting grating are arranged mutually displaced from the grating bars of the second X-ray converting grating in the direction perpendicular to the incident X-ray radiation, and
wherein the first X-ray converting grating and the second X-ray converting grating are arranged between two detectors configured to detect light or charge converted by the respective first and second X-ray converting gratings.

14. The method according to claim 13, wherein the structuring and filling is done from only a first side of the wafer, and wherein the structuring comprises an etching.

15. A non-transitory computer-readable medium having one or more executable instructions stored thereon, which when executed by a processor, cause the processor to perform a method for manufacturing an analyzing grid, comprising:
structuring a number of wafers to obtain an array of grating bars in each wafer, and
filling a space between the grating bars with X-ray converting material to obtain a number of X-ray converting gratings,
wherein the X-ray converting gratings are configured to form an analyzing grid for phase contrast imaging and/or dark-field imaging,
wherein the X-ray converting gratings are configured to convert incident X-ray radiation into light or charge,
wherein the X-ray converting gratings comprise at least a first X-ray converting grating and a second X-ray converting grating,
wherein each of the X-ray converting gratings comprises the array of grating bars,
wherein the grating bars within each of the X-ray converting gratings are arranged mutually displaced from each other in a direction perpendicular to an incident X-ray radiation by a specific displacement pitch, which is a distance between center lines of two adjacent grating bars,
wherein the grating bars of the first X-ray converting grating are arranged mutually displaced from the grating bars of the second X-ray converting grating in the direction perpendicular to the incident X-ray radiation, and
wherein the first X-ray converting grating and the second X-ray converting grating are arranged between two detectors configured to detect light or charge converted by the respective first and second X-ray converting gratings.

* * * * *